United States Patent
Ächtner et al.

(10) Patent No.: US 10,238,588 B2
(45) Date of Patent: Mar. 26, 2019

(54) AQUEOUS OXIDIZING COMPOSITION FOR HAIR

(71) Applicant: KAO GERMANY GMBH, Darmstadt (DE)

(72) Inventors: Anja Ächtner, Mannheim (DE); Axel Balke, Mühltal (DE); Ovidiu Feier-Iova, Darmstadt (DE); Carsten Häckl, Darmstadt (DE); Clarissa Lipinski, Darmstadt (DE); Jonathan Wood, Weinheim (DE)

(73) Assignee: KAO GERMANY GMBH, Darmstadt (DE)

( * ) Notice: Subject to any disclaimer, the term of this patent is extended or adjusted under 35 U.S.C. 154(b) by 0 days.

(21) Appl. No.: 14/898,554

(22) PCT Filed: Dec. 13, 2013

(86) PCT No.: PCT/EP2013/076478
§ 371 (c)(1),
(2) Date: Dec. 15, 2015

(87) PCT Pub. No.: WO2015/180739
PCT Pub. Date: Dec. 3, 2015

(65) Prior Publication Data
US 2016/0136064 A1    May 19, 2016

(30) Foreign Application Priority Data

Dec. 20, 2012    (EP) .................................... 12198682

(51) Int. Cl.
| | | |
|---|---|---|
| *A61K 8/22* | (2006.01) | |
| *A61K 8/31* | (2006.01) | |
| *A61K 8/49* | (2006.01) | |
| *A61K 8/46* | (2006.01) | |
| *A61Q 5/10* | (2006.01) | |
| *A61K 8/368* | (2006.01) | |
| *A61K 8/34* | (2006.01) | |
| *A61K 8/41* | (2006.01) | |

(52) U.S. Cl.
CPC .................. *A61K 8/22* (2013.01); *A61K 8/31* (2013.01); *A61K 8/34* (2013.01); *A61K 8/342* (2013.01); *A61K 8/345* (2013.01); *A61K 8/368* (2013.01); *A61K 8/411* (2013.01); *A61K 8/415* (2013.01); *A61K 8/416* (2013.01); *A61K 8/463* (2013.01); *A61K 8/4946* (2013.01); *A61K 8/4953* (2013.01); *A61Q 5/10* (2013.01); *A61K 2800/4322* (2013.01); *A61K 2800/49* (2013.01); *A61K 2800/596* (2013.01); *A61K 2800/882* (2013.01)

(58) Field of Classification Search
CPC . A61K 8/22; A61K 8/31; A61K 8/342; A61K 8/345; A61K 8/463; A61K 8/34; A61K 8/368; A61K 8/411; A61K 8/415; A61K 8/416; A61K 8/4946; A61K 8/4953; A61Q 5/10
See application file for complete search history.

(56) References Cited

U.S. PATENT DOCUMENTS

| | | | |
|---|---|---|---|
| 2003/0000026 A9 | 1/2003 | Laurent | |
| 2010/0146716 A1 | 6/2010 | Yamaguchi et al. | |
| 2011/0104092 A1* | 5/2011 | Panten | C11B 9/0019 424/65 |
| 2011/0318293 A1 | 12/2011 | Kleen et al. | |
| 2012/0207689 A1* | 8/2012 | Konno | A61K 8/046 424/62 |

FOREIGN PATENT DOCUMENTS

| | | |
|---|---|---|
| DE | 10 2009 001484 A1 | 9/2010 |
| FR | 2 942 704 A1 | 9/2010 |
| WO | 2012028456 A2 | 3/2012 |
| WO | WO 2012/032671 * | 3/2012 |
| WO | 2012/095397 A2 | 7/2012 |
| WO | 2012/095398 A2 | 7/2012 |

OTHER PUBLICATIONS

International Search Report and Written Opinion of the ISA dated Sep. 25, 2015, mailed Oct. 6, 2015.

* cited by examiner

*Primary Examiner* — Johann R Richter
*Assistant Examiner* — Genevieve S Alley
(74) *Attorney, Agent, or Firm* — Norris McLaughlin PA

(57) ABSTRACT

Present invention relates to an aqueous oxidizing composition for hair which makes possible achieving homogeneous coloration of multiple damaged hair and especially provides excellent grey coverage with oxidative hair dyes. The object of the invention is an aqueous oxidizing composition for hair comprising one or more oxidizing agent, one or more polyol, one or more oil, one or more solid fatty alcohol and one or more surfactant wherein fatty alcohol to oil weight ratio is less than 1, weight ratio of surfactant to sum of fatty alcohol and oil is less than 0.25 and polyol concentration is less than or equal to 2% by weight calculated to the total of the composition.

18 Claims, No Drawings

AQUEOUS OXIDIZING COMPOSITION FOR HAIR

This application is a § 371 U.S. National stage of PCT International Patent Application No. PCT/EP2013/076478, filed Dec. 13, 2013, which claims foreign priority benefit of European Patent Application No. EP 12198682.2, filed Dec. 20, 2012, the disclosures of each of which patent applications are incorporated herein by reference.

Present invention relates to an aqueous oxidizing composition for hair which makes possible achieving homogeneous coloration of multiple damaged hair and especially provides excellent grey coverage with oxidative hair dyes.

Oxidative hair dyeing has been known for many years. Among targets of oxidative hair dyeing, achieving homogeneous coloration and grey coverage have been particularly important. There are many patent publications and also many products available in mass and professional markets promising customers to achieve such results. Some of them are citing alkalinity to be an important factor and the others relate to dyestuff concentration in the dyeing composition. The results are not always satisfactory and therefore there is a clear need for new techniques to achieve homogeneous colors and especially to improve grey coverage of oxidative dyeing compositions, especially based on oxidative dye precursors.

The inventors of the present invention made observation that the homogenous hair coloring and improved grey coverage is indeed achieved when oxidizing compositions content is adjusted carefully. It has unexpectedly and surprisingly been found out that an aqueous oxidizing composition comprising one or more polyol, one or more oil, one or more solid fatty alcohol and one or more surfactant delivers improved homogeneous coloration and improved grey coverage.

Accordingly first object of the present invention is an aqueous oxidizing composition for hair comprising one or more oxidizing agent, one or more polyol, one or more oil, one or more solid fatty alcohol and one or more surfactant wherein fatty alcohol to oil weight ratio is less than 1, weight ratio of surfactant to sum of fatty alcohol and oil is less than 0.25 and polyol concentration is less than or equal to 2% by weight calculated to the total of the composition.

The second object of the present invention is the use of the aqueous oxidizing composition of the present invention for homogeneous coloring hair and/or for improved grey coverage of an oxidative dyeing composition.

The third object of the present invention is a process for coloring hair wherein the oxidizing composition of the present invention is mixed with a composition comprising one or more hair dyes and applied onto hair and after leaving on the hair for 1 to 45 min, rinsed off from hair and optionally hair is shampooed.

The fourth object of the present invention is a process for coloring hair wherein the oxidizing composition of the present invention is mixed with a composition comprising one or more oxidative dye precursors and having an alkaline pH and applied onto hair and after leaving on the hair for 1 to 45 min, rinsed off from hair and optionally hair is shampooed.

The fifth object of the present invention is a kit for coloring hair comprising to or more products wherein one of the products is the aqueous oxidizing composition of the present invention.

Aqueous oxidizing composition of the present invention comprises at least one oxidizing agent. Suitable non limiting examples are hydrogen peroxide, urea peroxide, melamine peroxide and sodium bromate. Most preferred is hydrogen peroxide. One or more oxidizing agents are comprised in the aqueous composition at a concentration of 1 to 20%, preferably 1 to 15% and more preferably 2 to 12% by weight calculated to the total of the composition.

The pH of the aqueous composition comprising one or more oxidizing agents is in the range of 2 to 5, preferably 2.5 to 4 and more preferably 3 to 4 whereas the pH of the composition comprising sodium bromate is preferably in the range of 6.5 to 7.5.

The aqueous oxidizing composition of the present invention comprises one or more polyol at a concentration less than but equal to 2%, preferably 1.75%, more preferably 1.5% and most preferably 1.25% and in particular 1% by weight calculated to the total of the composition. The term polyol means any compound having 2 or more hydroxyl groups in its molecule. Suitable non-limiting examples are glycerin, 1,2-propylene glycol, polyglycerins with 2 to 10 glycerin units, panthenol, glycol, butyleneglycol, 1,2-butanediol, 1,4, butanediol, 2,3-butanediol, pentylene glycol and 1,5-pentanediol. Preferred are glycerin, 1,2-propylene glycol, glycol, butyleneglycol 1,2-butanediol, 1,4, butanediol, 2,3-butanediol, and panthenol. More preferred are glycerin, 1,2-propylene glycol, glycol, butyleneglycol, and panthenol. Most preferred are glycerine, 1,2-propylene glycol, and panthenol and particularly preferred polyol is glycerin.

The composition of the present invention comprises one or more oil. Suitable oil components are those are liquid at room temperature i.e. 20° C. Suitable ones are synthetic and natural oils. Synthetic oils are silicones especially those of nonvolatile ones such as dimethicones with viscosity of 50 to 350 cSt measured by capillary viscosimeter and at 20° C., fatty acid fatty alcohol esters according to the general structure

wherein $R_1$ is a straight or branched, saturated or unsaturated alkyl with 11 to 21 C atomes and $R_2$ is a straight or branched, saturated or unsaturated alkyl with 1 to 22 C atomes such as behenyl behenate, behenyl isostearte, butyl stearate, butyl oleate, butyl myristate, butyloctyl oleate, cetyl palmitate, cetyl myristate, cetyl oleate, cetyl caprylate, cetyl caprate, decyl oleate, decyl cocoate, decyl isostearate, ethylhexyl myristate, ethyl hexyl laurate, ethyl hexyl oleate, ethyl isostearte, ethyl laurate, ethyl linoleate, ethyl myristate, ethyl oleate, ethyl palmitate, ethylricinoleate, ethyl stearate, hexyl isostearat, hexyl laurate, hexyl myristate, hexyl stearate, hexyl decyl oleate, isobutyl laurate, isobutyl myristate, isobutyl palmitate, isobutyl stearate, isocetyl behenate, isobutyl laurate, isobutyl oleate, isobutyl stearate, isobutyl cocoate, isohexyl caprate, isopropyl palmitate, isopropyl stearate, isopropyl behenate, isopropyl laurate, isopropyl oleate, isopropyl ricinoleate and isopropyl palmitate, fatty alcohol ethers according to general structure

wherein $R_3$ and $R_4$ are same or different, straight or branched, saturated or unsaturated alkyl with 8 to 22 C atoms such as dicetyl ether, dimyristyl ether, dicyprylyl ether and dodecyl ether.

Natural oils are such as mineral oil and plant derived oils such as avocado oil, olive oil, almond oil, peach oil, passiflora oil, black cumin oil, borage oils, evening primrose oil, grapeseed oil, hempseed oil, kukui nut oil, rosehip oil, safflower oil, walnut oil and weatgerm oil. The most preferred is mineral oil.

Concentration of oil in the oxidizing compositions of the present invention is in the range of 0.5 to 10%, preferably 0.5 to 7.5% and more preferably 0.75 to 5% and most preferably 1 to 4% by weight calculated to the total of the composition.

The oxidizing composition of the present invention comprises one or more fatty alcohol solid at room temperature, i.e. 20° C. Suitable ones are those straight unsaturated fatty alcohols with 14 to 22 C atoms in their alkyl chains. Suitable ones are myristyl alcohol, cetyl alcohol, stearyl alcohol, arachidyl alcohol and behenyl alcohol and their mixtures. The most preferred is cetaryl alcohol which is the mixture of cetyl and stearyl alcohol.

Concentration of fatty alcohol in the oxidizing compositions of the present invention is in the range of 0.4 to 9.9%, preferably 0.4 to 7.4% and more preferably 0.74 to 4.9% and most preferably 0.9 to 3.9% by weight calculated to the total of the composition.

The composition of the present invention comprises one or more surfactants. Suitable ones are anionic, non-ionic, amphoteric and cationic surfactants. Preferred are anionic and cationic ones and most preferred are anionic surfactants.

Total concentration of the surfactants varies in the range of 0.05% to 4.9%, preferably 0.075 to 3.9%, more preferably 0.08 to 2.9 and most preferably 0.09% to 1.95% by weight, calculated to total composition.

Non-limiting suitable anionic surfactants are especially the known alkyl sulphates and alkyl ether sulfates, carboxylic acids, in particular in form of their alkali salts, as well as protein fatty acid condensates, fatty acid salts, alkyl/alkenyl succinates, anionic amino acid surfactants especially glutames such as sodium lautoyl glutamate. The preferred anionic surfactants are alkyl sulphates and alkyl ether sulphates and the most preferred is alkyl sulphate types and their salts and in particular sodium lauryl sulphate.

Suitable nonionic surfactants are in particular $C_8$-$C_{18}$-fatty alcohol polyglycol ethers such as ceteareth-20, laureth-16, ceteth-30, fatty acid polyglycol esters, fatty acid alkanolamides, aminoxides, and especially $C_8$-$C_{18}$-alkyl polyglucosides.

Also possible is the incorporation of amphoteric surfactants, such as the known alkyl betaines, alkyl amido betaines, and alkyl amphoacetates. Examples of the amphoteric surfactant include carbobetaine, amidobetaine, sulfobetaine, hydroxyl sulfobetaine, amidosulfobetaine, phospho-betaine, and imidazolinium surfactants having an alkyl group, an alkenyl group, or an acyl group having 8 to 24 carbon atoms.

Cationic surfactants especially mono alkyl quaternary ammonium slats of the following general structure

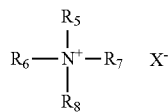

where $R_5$ is a saturated or unsaturated, branched or non-branched alkyl chain with 8-22 C atoms or

where $R_9$ is saturated or unsaturated, branched or non-branched alkyl chain with 7-21 C atoms and n has typical value of 1-4 or

where $R_{10}$ is saturated or unsaturated, branched or non-branched alkyl chain with 7-21 C atoms and n has typical value of 1-4, and and $R_6$, $R_7$ and $R_8$ are independent from each other H or lower alkyl chain with 1 to 4 carbon atoms, and X is an anion such as chloride, bromide or methosulfate.

Suitable non-limiting examples are cetrimonium chloride, steartrimonium chloride and behentrimonium chloride.

The compositions of the present invention comprise surfactant, fatty alcohol and oil components at a specific weight ratio. The weight ratio of the surfactant to total of fatty alcohol and oil content is 0.25, preferably 0.2 and more preferably 0.15 and most preferably 0.1.

The compositions of the present invention may furthermore comprise additional compounds such as stabilizing compounds for oxidizing agent especially for hydrogen peroxide, chelating agents, and buffering agents such as phosphoric acid and its salts and fragrance.

The composition of the present invention is mixed with a composition comprising at least one hair dye (Dye composition) prior to application onto hair.

Suitable hair dyes are direct dyes such as anionic, cationic and neutral nitro dyes. Preferred are cationic and neutral nitro dyes and their mixtures.

Suitable direct dyes are selected from cationic, anionic, neutral nitro dyes and their mixtures. Preferred are cationic and neutral nitro dyes and their mixtures.

Any cationic direct dye is in principal suitable for the compositions. Examples are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Orange 31, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87.

Any anionic dye is in principal suitable for the compositions. Suitable examples are such as Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Among those, the preferred anionic dyestuffs are Acid Red 52, Acid Violet 2, Acid Red 33, Acid Orange 4, Acid Red 27 and Acid Yellow 10 and their salts. The most preferred anionic dyes are Acid Red 52, Acid Violet 2, Acid Red 33, Acid Orange 4 and Acid Yellow 10, and their salts Neutral dyes, so called nitro dyes for shading purposes are also optionally contained in the compositions. Suitable ones are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Concentration of one or more direct dyes in total is in the range of 0.001 to 10% by weight, preferably 0.01 to 7.5% more preferably 0.05 to 5%, most preferably 0.1 to 3% by weight calculated to total of the dye composition.

The dye composition comprises additionally or only oxidative dye precursors and an alkalizing agent.

Suitable examples to the oxidative dye precursors are p-phenylenediamine, p-methylaminophenol and substituted p-phenylenediamines such as 2,5-diamino-toluene, 2-n-propyl or 2-ethyl-p-phenylenediamine, 2,6-di-methyl-p-phenylene-diamine, 2-(2,5-diaminophenyl) ethanol, 1-amino-4-bis-(2'-hydroxy-ethyl)amino-benzene, 2-(2-hydroxyethyl amino)-5-aminotoluene, 4,4'-diaminodiphenylamine, 4-aminodiphenylamine, 2-amino-5-N, N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, pyrazole and the derivatives thereof such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetraamino pyrimidines, triaminohydroxy pyrimidines, diaminomono- and -dihydroxy pyrimidines, aminotriazines, 5-amino salicylic acid and/or 1,2,4-triamino benzene or the water-soluble salts thereof.

Further suitable aminopyridines are 2,5-diaminopyridine, 2,3-diaminopyridine, 2,6-diaminopyridine, 3-amino-2-methyl amino-6-methoxypyridine, 2-dimethyl-5-aminopyridine, 2-dimethyl aminoethyl-3-hydroxypyridine, 2-amino-4,6-dimethyl pyridine, 2-amino-3-hydroxypyridine, 3-amino-2(β-hydroxyethyl amino)-6-methoxypyridine, 2,6-dimethyl amino-5-aminopyridine, 2-di(hydroxyethyl)amino-5-aminopyridine, 2-hydroxyethyl amino-5-aminopyridine, 4-hydroxy-2,5,6-triaminopyrimidine and/or the water-soluble salts thereof.

Further, Indole and indoline derivatives can as well be contained in the colouring composition of the present invention. Examples to those are: 6-aminoindol, 6-hydroxyindole, 1-ethyl-6-hydroxyindole, 1-methyl-4-hydroxyindol, 1-methyl-6-hydroxyindole, 2-methyl-6-hydroxyindole, 5-hydroxyindol, 4-hydroxyindol, 5,6-dihydroxyindole, 6-aminoindoline, 6-hydroxyindoline, 1-ethyl-6-hydroxyindoline, 1-methyl-4-hydroxyindoline, 1-methyl-6-hydroxyindoline, 2-methyl-6-hydroxyindoline, 5-hydroxyindoline, 4-hydroxyindoline, 5,6-dihydroxyindoline and their respective salts.

Suitable coupling agents are resorcinol, 2-methyl resorcinol, 4-chlororesorcinol, 2-amino-4-chlorophenol, 5-amino-4-methoxy-2-methylphenol, 3-amino-phenol, 1-methyl-2-hydroxy-4-aminobenzene, 3-N,N-dimethyl aminophenol, 2.6-dihydroxy-3.5-dimethoxypyridine, 5-amino-3-methylphenol, 6-amino-3-methylphenol, 3-amino-2-methylamino-6-methoxypyridine, 2-amino-3-hydroxy-pyridine, 2-dimethyl-amino-5-aminopyridine, 2,6-diaminopyridine, 1,3-diamino-benzene, 1-amino-3-(2'-hydroxyethylamino)benzene, 1-amino-3-[bis(2'-hydroxyethyl)amino]benzene, α-naphthol, 4,6-dichlororesorcinol, 1,3-diamino-toluene, 1-hydroxy naphthalene, 4-hydroxy-1, 2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof. 5-amino-2-methylphenol, 2-methyl-5-hydroxyethylaminophenol, 2,4-diamnophenoxyethanol, 2-amino-4-hydroxyethylaminoanisol, 2-methyl-5-amino-6-chlorophenol, 1,3-bis(2,4-diaminophenoxy)propane, 2-bis (2-hydroxyethyl)aminotoluene, 2-amino-5-methylphenol or the water-soluble salts thereof.

Concentration of one or more oxidative dyes in total— total concentration of precursors and couplers, if present—is in the range of 0.001 to 10% by weight, preferably 0.01 to 7.5% more preferably 0.05 to 5%, most preferably 0.1 to 3% by weight calculated to total of the dye composition.

The dye composition comprises one or more alkalizing agent. Suitable are sodium or potassium hydroxide, ammonia, alkanol amines such as monoethanolamine, carbonates such as ammonium carbonate, potassium carbonate, ammonium bicarbonate and ammonium chloride. Concentration of one or more alkalizing agents in total is in the range of 1 to 10% by weight calculated to the total composition. The most preferred are ammonia and monoethanolamine.

pH of the dye composition varies in the range of 2 to 11, preferably 6 to 10.5, more preferably 6.5 to 10.

Any of the compositions described above, the aqueous oxidizing composition and/or dyeing compositions comprising direct dyes and/or oxidative dye precursors may further comprise one or more of the compounds described below.

Further, the above mentioned compositions may comprise additional cationic polymer. Basically suitable are all cationic polymers listed under the generic name "Polyquaternium" in the CTFA International Cosmetic Ingredient Dictionary. Examples are Polyquaternium 6, Polyquaternium 7, Polyquaternium 10, Polyquaternium 11, Polyquaternium 22 and Polyquaternium 28, Polyquaternium 39, Polyquaternium 16 and Polyquaternium 87.

The cationic polymers also include the quaternized products of graft polymers from organopolysiloxanes and polyethyl oxazolines described in EP-A 524 612 and EP-A 640 643. Such polymer is known with its CTFA name Polysilicone-9.

Concentration of one or more additional cationic polymers is in the range from 0.05% to 2.5%, preferably 0.1% to 1.5% by weight, calculated to total each composition.

Further the above mentioned composition may comprise one or more organic solvent. Suitable organic solvents are 2-methyl-1,3-propanediol, mono and dialcohols or the ethers thereof, in particular mono-$C_1$-$C_3$-alkyl ether, ethanol, n-propanol, isopropyl alcohol, 1-methoxypropanol, 1-ethoxypropanol and ethoxydiglycol, diols and their esters 1,3- and 1,4-butanediol, diethyleneglycol and the monomethyl and monoethyl ether thereof, dipropylene glycol and the monomethyl and monoethyl ether thereof, glycerol, hexanetriol, ethyl carbitol, benzyl alcohol, benzyloxy ethanol, propylene carbonate, N-alkyl pyrrolidone, and urea or their mixture preferably in an amount from about 0.1% to 10% by weight, calculated to the total of each composition.

The above mentioned compositions can comprise further ceramide type of compound such as cetyl-PG-hydroxyethylpalmitamide.

Further optional ingredient are sterols, especially the phytosterols are useful hair restructuring compounds can be present in the above mentioned compositions. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

In a further preferred embodiment of the present invention, compositions may comprises at least one diamine compound. Preferred diamide compounds are according to the general structure

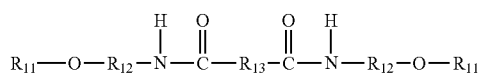

wherein $R_{11}$ is a linear or branched, saturated or unsaturated alkyl chain with 1 to 12 C atoms which may be substituted with hydroxy and/or alkoxy groups, preferably $R_{11}$ is linear or branched, saturated or unsaturated alkyl chain with 1 to 12 C atoms which may be substituted by 1 to 3 substituents selected from a hydroxy group and C1 to C6 alkoxy group, more preferably $R_{11}$ is a unsubstituted alkyl group with 1 to 12 C atoms, and alkyl group with 2 to 12 C atoms substituted by one or two hydroxyl groups, by one alkoxy group with 1 to 6 C atoms or by one hydroxyl and one alkoxy group with 2 to 6 C atoms, $R_{12}$ is linear or branched alkyl chain with 1 to 5 C atoms, preferably linear or branched alkyl chain with 2 to 5 C atoms and more preferably an alkyl chain with 2 to 3 C atoms, and $R_{13}$ linear or branched, saturated or unsaturated alkyl chain with 1 to 22 C atoms, preferably linear or branched, saturated or unsaturated alkyl chain with 11 to 22 C atoms.

Preferred individual diamide compounds are the ones according to the formula A to G.

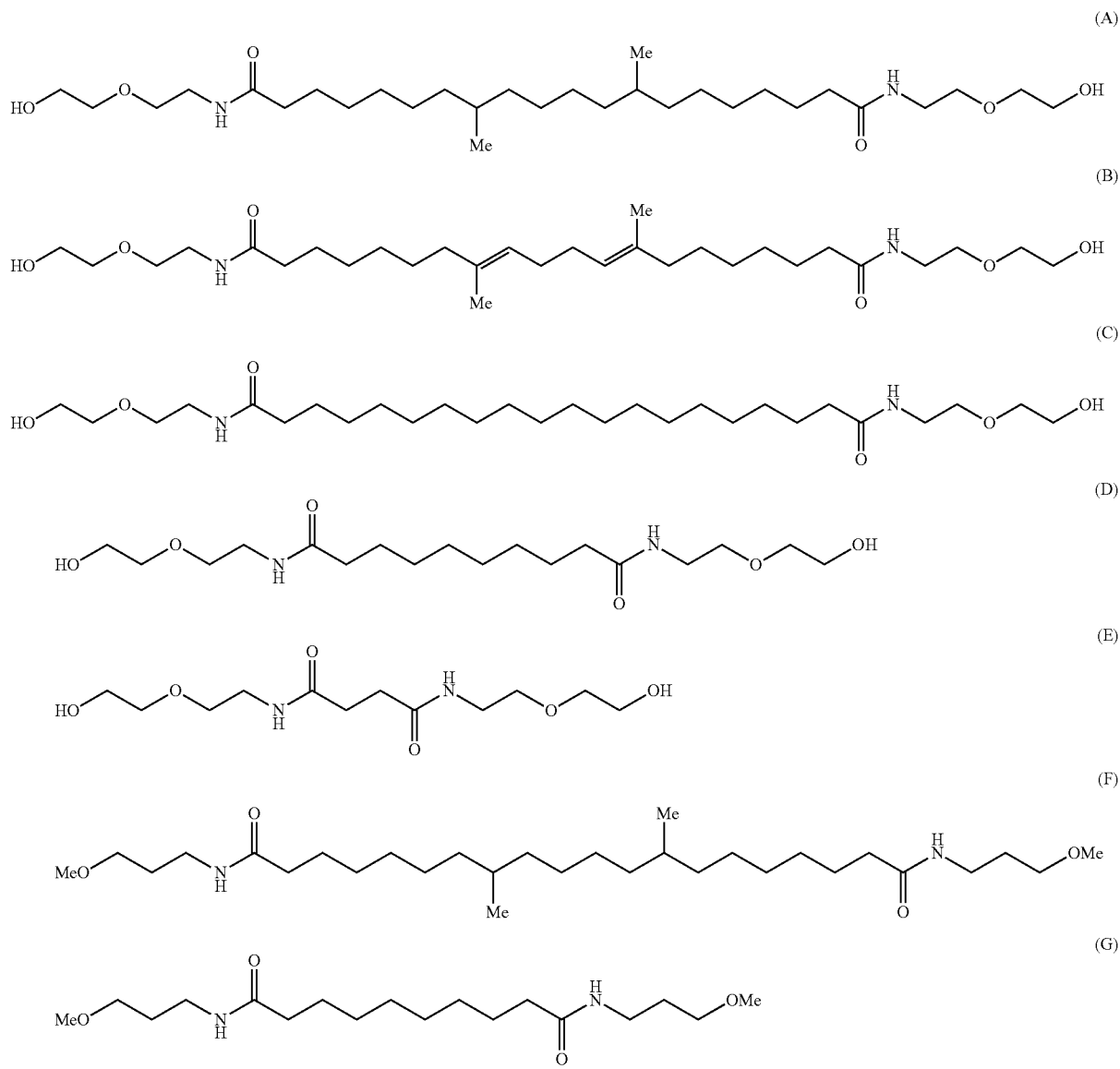

Particularly preferred diamide compound is the compound F which is bis(methoxypropylamido)isodocosane and commercially available from Kao Corporation—Japan.

Concentration of diamide compounds in the intermediate treatment compositions of the present invention is in the range of 0.001 to 5%, preferably 0.002 to 3% more preferably 0.005 to 2% and most preferably 0.01 to 1% by weight calculated to total of each composition.

Further additional compounds may be present in the above mentioned compositions of the present invention is ubichinone of the formula

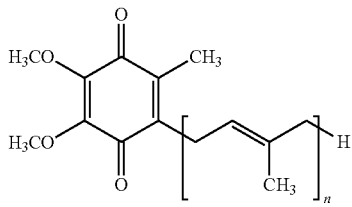

where n is a number between 1 and 10. Preferred ubichinones are the ones where n is a number between 6 and 10 and especially preferred is Ubichinone 50 where n is 10, also known as Coenzyme Q10. Concentration ubichinone of the above formula in the compositions is from 0.0001 to 1%, preferably from 0.0002 to 0.75%, more preferably from 0.0002 to 0.5% and most preferably from 0.0005 to 0.5% by weight, calculated to total composition.

The following examples are to illustrate but not to limit the invention.

EXAMPLE 1

|  | % by weight |
|---|---|
| Oxidizing composition |  |
| Cetearyl alcohol | 2.0 |
| Mineral oil | 2.5 |
| Sodium lauryl sulphate | 0.2 |
| Glycerin | 0.9 |
| Hydrogen peroxide | 6.0 |
| Salicylic acid | 0.05 |
| Phosphoric acid/sodium phosphate | q.s. to pH 2.1 |
| Water | to 100 |
| Dyeing composition |  |
| Decyl glucoside | 0.1 |
| Sodium laureth sulphate | 0.1 |
| Polyquaternium - 7 | 0.5 |
| Sodium sulphite | 0.5 |
| Ascorbic acid | 0.5 |
| Monoethanol amine | 4.0 |
| Ammonium hydroxide | 4.0 |
| EDTA di sodium salt | 0.5 |
| Ethanol | 10.0 |
| 4-amino-m-cresol | 0.35 |
| 4-amino-2-hydroxytoluene | 0.2 |
| 2-Hydroxyethyl-p-phenylenediamine sulfate | 0.15 |
| m-aminophenol | 0.1 |
| Resorcinol | 0.2 |
| 2,5,6-triamino-4-pyrimidinol sulphate | 0.05 |
| 2-amino-6-chloro-4-nitrophenol | 0.11 |
| Fragrance | 0.5 |
| Water | q.s. to 100 | pH of the above composition was 9.8.

The above oxidizing and dyeing compositions were mixed at a weight ratio of 1:1 and the mixture had a pH of 9.8.

Partial grey and damaged hair was dyed with the above compositions. It was observed that the hair was dyed homogeneously and grey coverage was 100%.

EXAMPLE 2

|  | % by weight |
|---|---|
| Oxidizing composition |  |
| Behenyl alcohol | 2.0 |
| Isopropyl myristate | 2.5 |
| Behentrimonium chloride | 0.2 |
| Panthenol | 0.9 |
| Hydrogen peroxide | 6.0 |
| Salicylic acid | 0.05 |
| Phosphoric acid/sodium phosphate | q.s. to pH 3.1 |
| Water | to 100 |
| Dyeing composition |  |
| 4-amino-m-cresol | 0.4 |
| 4-amino-2-hydroxytoluene | 0.2 |
| 2-Hydroxyethyl-p-phenylenediamine sulfate | 0.15 |
| m-aminophenol | 0.1 |
| Resorcinol | 0.2 |
| Basic red 51 | 0.5 |
| Basic orange 31 | 0.5 |
| Basic yellow 87 | 0.2 |
| HC red 3 | 0.5 |
| Ammonium hydroxide | 8.0 |
| Ceteareth-30 | 0.2 |
| Water | to 100 | pH of the above composition was 9.8.

The above oxidizing and dyeing compositions were mixed at a weight ratio of 1:1 and the mixture had a pH of 9.5.

Partial grey and damaged hair was dyed with the above compositions. It was observed that the hair was dyed homogeneously and grey coverage was 100%.

The invention claimed is:
1. An aqueous oxidizing composition for hair comprising:
   (a) one or more oxidizing agent,
   (b) one or more polyol selected from the group consisting of glycerin, 1,2-propylene glycol, polyglycerins with 2 to 10 glycerin units, panthenol, glycol, butyleneglycol, 1,2-butanediol, 1,4-butanediol, 2,3-butanediol, pentylene glycol and 1,5-pentanediol,
   (c) one or more oil selected from the group consisting of synthetic oils and natural oils,
   (d) one or more fatty alcohol which is solid at room temperature (20° C.), and
   (e) one or more surfactant selected from the group consisting of anionic, amphoteric and cationic surfactants,
   wherein
   (i) fatty alcohol to oil weight ratio is less than 1,
   (ii) weight ratio of surfactant to sum of fatty alcohol and oil is less than 0.25,
   (iii) oil concentration is 0.5 to 10% by weight calculated to the total of the composition, and
   (iv) polyol concentration is less than or equal to 2% by weight, calculated to the total of the composition.
2. The composition according to claim 1, wherein the one or more oxidizing agent is hydrogen peroxide.
3. The composition according to claim 2, wherein the hydrogen peroxide is present at a concentration of 1 to 20% by weight calculated to the total of the compositions.
4. The composition according to claim 2, having a pH between 2 and 5.

5. The composition according to claim 1, comprising glycerine as the sole polyol.

6. The composition according to claim 1, wherein the one or more oil is liquid at room temperature.

7. The composition according to claim 1, comprising mineral oil as the sole oil component.

8. The composition according to claim 1, wherein the one or more fatty alcohol is selected from myristyl alcohol, cetyl alcohol, stearyl alcohol, arachidyl alcohol, behenyl alcohol and mixtures thereof.

9. The composition according to claim 8, wherein the one or more fatty alcohol is present at a concentration of 0.4 to 9.9% by weight calculated to the total of the composition.

10. The composition according to claim 1, wherein the one or more surfactant is anionic surfactant.

11. The composition according to claim 10, wherein the one or more surfactant is sodium lauryl sulfate.

12. The composition according to claim 1, wherein the one or more surfactant is selected from quaternary ammonium compounds of the general structure

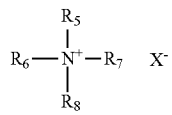

where $R_5$ is a saturated or unsaturated, branched or non-branched alkyl chain with 8-22 C atoms, or

where $R_9$ is saturated or unsaturated, branched or non-branched alkyl chain with 7-21 C atoms and n has typical value of 1- 4, or

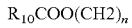

where R10 is saturated or unsaturated, branched or non-branched alkyl chain with 7-21 C atoms and n has typical value of 1-4, and
and $R_6$, $R_7$ and $R_8$ are independent from each other H or lower alkyl chain with 1 to 4 carbon atoms, and X is an anion.

13. The composition according to claim 1, wherein the one or more surfactant is present at a concentration of 0.05 to 4.9% by weight calculated to the total of the composition.

14. An aqueous oxidizing composition for hair comprising:
(a) one or more oxidizing agent,
(b) one or more polyol selected from the group consisting of glycerin, 1,2-propylene glycol, polyglycerins with 2 to 10 glycerin units, panthenol, glycol, butyleneglycol, 1,2-butanediol, 1,4-butanediol, 2,3-butanediol, pentylene glycol and 1,5-pentanediol,
(c) one or more oil selected from the group consisting of synthetic oils and natural oils,
(d) one or more fatty alcohol which is solid at room temperature (20° C.), and
(e) one or more surfactant selected from the group consisting of anionic, amphoteric and cationic surfactants,
wherein
(i) fatty alcohol to oil weight ratio is less than 1,
(ii) weight ratio of surfactant to sum of fatty alcohol and oil is less than 0.25,
(iii) oil concentration is 0.5 to 10% by weight calculated to the total of the composition, and
(iv) polyol concentration is less than 1% by weight, calculated to the total of the composition.

15. A process for coloring hair comprising:
a) mixing the oxidizing composition according to claim 1 with a composition comprising one or more hair dye,
b) applying onto hair a mixture obtained from step a),
c) leaving the mixture obtained from step a) on hair for 1 to 45 min,
d) rinsing off from hair the mixture obtained from step a).

16. The process according to claim 15, wherein the one or more hair dye is a direct dye.

17. A process for coloring hair comprising:
a) mixing the oxidizing composition according to claim 1 with a composition comprising one or more oxidative dye precursors having an alkaline pH,
b) applying onto hair a mixture obtained from step a),
c) leaving the mixture obtained from step a) on hair for 1 to 45 min,
c) rinsing off from hair the mixture obtained from step a).

18. A kit for dyeing hair comprising two or more products, wherein one of the two or more products is the aqueous oxidizing composition according to claim 1.

* * * * *